United States Patent
Franklin et al.

(12) 
(10) Patent No.: US 6,459,927 B1
(45) Date of Patent: Oct. 1, 2002

(54) CUSTOMIZABLE FIXTURE FOR PATIENT POSITIONING

(75) Inventors: Ronald J. Franklin, Bowdoinham; Joel I. Franck, Durham; Frederick C. Haer, Brunswick, all of ME (US)

(73) Assignee: Neutar, LLC, Bowdoinham, ME (US)

( * ) Notice: Subject to any disclaimer, the term of this patent is extended or adjusted under 35 U.S.C. 154(b) by 80 days.

(21) Appl. No.: 09/698,294

(22) Filed: Oct. 27, 2000

Related U.S. Application Data

(63) Continuation-in-part of application No. 09/110,070, filed on Jul. 6, 1999.
(60) Provisional application No. 60/162,721, filed on Oct. 29, 1999.

(51) Int. Cl.[7] .............................................. A61B 5/055
(52) U.S. Cl. ...................... 600/429; 606/130; 600/417; 378/205
(58) Field of Search ................................ 600/417, 429; 606/130; 378/205

(56) References Cited

U.S. PATENT DOCUMENTS

| | | |
|---|---|---|
| 4,256,112 A | 3/1981 | Kopf et al. |
| 4,805,615 A | 2/1989 | Carol |
| 5,107,839 A | 4/1992 | Houdek et al. |
| 5,116,345 A | 5/1992 | Jewell et al. |
| 5,222,499 A | 6/1993 | Allen et al. |
| 5,263,956 A | 11/1993 | Nobels |
| 5,298,115 A | 3/1994 | Leonard |
| 5,300,076 A | 4/1994 | Leriche |
| 5,370,692 A | 12/1994 | Fink et al. |
| 5,397,329 A | 3/1995 | Allen |
| 5,531,229 A | 7/1996 | Dean et al. |
| 5,595,703 A | 1/1997 | Swaelens et al. |
| 5,627,949 A | 5/1997 | Letcher, Jr. |
| 5,638,819 A | 6/1997 | Manwaring et al. |
| 5,682,890 A | * 11/1997 | Kormos et al. ............. 600/417 |
| 5,702,406 A | 12/1997 | Vilsmeier et al. |
| 5,728,106 A | 3/1998 | Misko et al. |
| 5,732,703 A | 3/1998 | Kalfas et al. |
| 5,741,215 A | 4/1998 | D'Urso |
| 5,752,962 A | 5/1998 | D'Urso |
| 5,768,134 A | 6/1998 | Swaelens et al. |

(List continued on next page.)

FOREIGN PATENT DOCUMENTS

| | | |
|---|---|---|
| WO | WO 95/13758 | 5/1995 |
| WO | WO 96/11624 | 4/1996 |
| WO | WO 00/01316 | 1/2000 |

OTHER PUBLICATIONS

Stratasys, Inc. FDM2000 Rapid Prototyping System Website Brochure.

*Primary Examiner*—Marvin M. Lateef
*Assistant Examiner*—Runa Shah Qaderi
(74) *Attorney, Agent, or Firm*—Fish & Richardson, P.C.

(57) ABSTRACT

A customized positioning fixture is fabricated specifically for a patient the purpose of positioning a portion, or all, of the patient's body relative to a medical apparatus. The customized positioning fixture is fabricated such that the relative position of the patent to the medical apparatus is predetermined before a procedure is performed on the patient using the apparatus. The positioning fixture is fabricated using a computer-aided or an automated computer-controlled process according to data determined for that patient, for example, using a rapid prototyping and tooling (RPT) technique. In some embodiments, the positioning fixture is designed to be repeatedly removed and reattached to the patient, thereby allowing the patient to be repeatedly precisely re-positioned in the medical device is separated sessions. A second positioning fixture can also be fabricated so that the patient can be positioned relative to a second apparatus in a way that the patient's position in the two different apparatuses is related in a desired manner.

18 Claims, 5 Drawing Sheets

U.S. PATENT DOCUMENTS

| | | |
|---|---|---|
| 5,776,143 A | 7/1998 | Adams |
| 5,807,252 A | 9/1998 | Hassfeld et al. |
| 5,823,778 A | 10/1998 | Schmitt et al. |
| 5,891,157 A | 4/1999 | Day et al. |
| 5,891,158 A | 4/1999 | Manwaring et al. |
| 5,967,982 A | 10/1999 | Barnett |
| 5,978,696 A | 11/1999 | VomLehn et al. |
| 5,980,535 A | 11/1999 | Barnett et al. |
| 5,987,349 A | 11/1999 | Schultz |
| 6,006,126 A | 12/1999 | Cosman |
| 6,011,987 A | 1/2000 | Barnett |
| 6,026,315 A | 2/2000 | Lenz et al. |
| 6,167,292 A * | 12/2000 | Badano et al. ............... 600/407 |
| 6,246,898 B1 * | 6/2001 | Vesely et al. ............... 600/424 |
| 6,275,723 B1 * | 8/2001 | Ferris et al. ................ 324/318 |

\* cited by examiner

CUSTOMIZABLE FIXTURE FOR PATIENT POSITIONING

CROSS-REFERENCE TO RELATED APPLICATIONS

This application is a continuation-in-part of U.S. application Ser. No. 09/110,070, filed Jul. 6, 1999. This application also claims the benefit of U.S. Provisional Application No. 60/162,721 filed Oct. 29, 1999. Both applications are incorporated herein by reference.

BACKGROUND

This invention relates to positioning a patient using a fixture that is customized for that patient.

In many medical procedures, it is desirable or necessary for a patient to be fixed in position (location and orientation) relative to a medical apparatus during the procedure. For example, a patient's head may be restrained during a scanning procedure in a device such as a CT or MRI scanner. After such a scanning procedure, a coordinate system of the scanned image is often mapped, or "registered," to a physical coordinate system to provide a way of physically locating features that are visible in the scanned image. Fiducial markers, which can be anatomical structures or devices attached to the body, serve as reference points for the physical coordinate system. If a subsequent scan is performed, for example using a different scanning technique, the multiple scans can be registered to a common physical coordinate system in order to view the same features in the different scanned images.

In some medical procedures, it is also desirable or necessary to repeatedly position a patient in a particular location and orientation relative to the medical apparatus on a number of separate occasions. For example, a patient may return on multiple days for radiation therapy (radiotherapy) in which a beam of radiation is directed toward a particular feature in the body (a "target") such as a cancerous tumor. One approach to targeting the same feature at each session is, at each session, to first restrain the patient relative to the apparatus and then to determine the location of the target relative to the apparatus, for example, using the locations of fiducial markers on patient. In one approach, a "bite plate" with trackable markers is used to determine the position of the patient relative to a medical apparatus using a remote sensing system. The medical apparatus is adjusted according to the sensed position of the patient. Another approach to targeting the same feature at each session is to restrain the patient in precisely the same position relative to the apparatus at each session. In one such approach, a complex, cumbersome, and often painful positioning device, such as a stereotactic head frame, is fixed to a patient prior to scanning. The device is left in place after scanning to later position or register the patient in the medical apparatus. In another approach to repeatable positioning, a molded synthetic cast of a patient's head is made, and split in half to allow removal and subsequent re-attachment to the head. A stereotactic frame is attached to the mold, thereby allowing repeatable positioning of the stereotactic frame. Features in the body are then targeted relative to the stereotactic frame.

SUMMARY

In one aspect, in general, the invention is a method for positioning a body in relation to a medical apparatus using a customized positioning fixture. Mounting data that characterizes positions of a number of mounting locations on the body is first determined. Using this mounting data, a digital model of the positioning fixture is computed. The digital model characterizes a shape of the positioning fixture such that the shape includes a first set of mounting structures that mate with the mounting locations on the body, and a second set of mounting structures for attaching the positioning fixture to the medical apparatus. The positioning fixture is then fabricated according to the digital model. The body is fixed to the medical apparatus in a predetermined position of the body relative to the medical apparatus. This involves mating the first set of mounting structures with the mounting locations on the body, and attaching the positioning fixture to the medical apparatus using the second set of mounting structures.

The invention can include one or more of the following features.

Fabricating the positioning fixture includes forming a unitary structure using a computer-controlled process. The unitary structure is formed using a rapid prototyping and tooling (RPT) technique.

The method includes, after fixing the body to the medical apparatus in the predetermined position, releasing the body from the positioning fixture. Then, the steps of fixing the body to and then releasing the body from the medical apparatus are repeated. At each repetition, the body is fixed in the same predetermined position relative to the medical apparatus.

The method includes forming a three-dimensional scanned image of the body. In order to determine the mounting data, the mounting locations are identified in the scanned image.

The method includes attaching a set of mounting devices to the body prior to forming the scanned image. These mounting devices form the mounting locations on the body to which the position fixture will be fixed. The mounting devices can include bone anchors, which can be subcutaneous bone anchors.

Identifying the mounting locations in the scanned image includes identifying points on an anatomical structure of the body to which the positioning fixture will be fixed.

The shape of the positioning fixture forms a number of separate segments that together form a clamp, or other structure which mates with the anatomical structure when the positioning fixture is fixed to the body.

The medical apparatus is a scanning device. For instance, the scanning device is a CT or an MRI scanner.

The method includes determining a location of a target within the body. Using the determined location of the target, the predetermined position of the body is determined in order to position the target at a predetermined position relative to medical apparatus when the body is fixed to the apparatus using the positioning fixture.

The medical apparatus includes a radiation therapy device.

The method includes determining a second position of the body relative to a second medical apparatus. The mounting data and the determined second position are used in computing a second digital model of a second positioning fixture. The second positioning fixture is fabricated according to the second digital model. The body is then fixed to the second medical apparatus in that second position. This involves mating the second positioning fixture with the mounting locations on the body and attaching the second positioning fixture to the second medical apparatus.

The invention includes one or more of the following advantages.

By providing a way of positioning the patient in a predetermined location and orientation relative to a medical apparatus, the actual location of the patient does not need to be determined once the patient is fixed in the medical apparatus. This has a first advantage of reducing the amount of time the patient is fixed to the apparatus. A second advantage is that the patient may be more accurately positioned than can be determined after the patient is fixed by a registration procedure.

By fabricating multiple fixtures based on a single scan of the patient, each adapted to a different medical apparatus such as to different scanning devices, the relative position of the patient in the different devices can be predetermined. For instance, if two scanning devices produce planar "slices" of images, then the relative position in the two scanners can be predetermined such that the slices from the two scanning devices are parallel.

By fabricating the customized fixture from a scanned image of the patient, rather than molding the fixture to the contours of the patient's body, the patient does not suffer the inconvenience and discomfort that may be associated with that molding process.

By not requiring that the customized fixture is attached during the initial scanning, a registration process is avoided by forming the customized fixture to not only mate with the patient but to also position a device, such as a stereotactic frame, in a predetermined position relative to the patient.

Other features and advantages of the invention are apparent from the following description, and from the claims.

DESCRIPTION

1 Overview

In various embodiments of the invention, a customized positioning fixture is fabricated specifically for a patient for the purpose of positioning a portion, or all, of the patient's body relative to a medical apparatus. The customized positioning fixture is fabricated such that the relative position of the patient to the medical apparatus is predetermined before the patient is secured to the apparatus and a medical procedure is performed. The positioning fixture is fabricated using a computer-aided or an automated computer-controlled process according to data determined for that patient. This data characterizes the geometry of mounting locations on the body to which the positioning fixture is to be attached during the procedure, and in some embodiments, identifies the location of a target on or within the patient's body relative to the mounting locations. The positioning fixture includes mounting structures that mate with the mounting locations on the body such that the positioning fixture can be firmly attached to the patient's body at the mounting locations. The positioning fixture also includes mounting structures that mate with mounting locations on the medical apparatus so that the positioning fixture can also be firmly attached to the medical apparatus. The relative locations of the mounting structures that mate with the body and those that mate with the medical device determine how the patient is positioned relative to the medical apparatus during the procedure. In some embodiments, the relative position is determined based on the location of a target in the body so that the target itself is located in a predetermined location relative to the medical apparatus. In some embodiments, the positioning fixture is designed to be repeatedly removed and reattached to the patient, thereby allowing the patient to be repeatedly precisely re-positioned in the medical device in separated sessions. In some embodiments, a second positioning fixture is also fabricated so that the patient can be positioned relative to a second apparatus in a way that the patient's position in the two different apparatuses is related in a desired manner.

2 Exemplary Application

Figure 5:
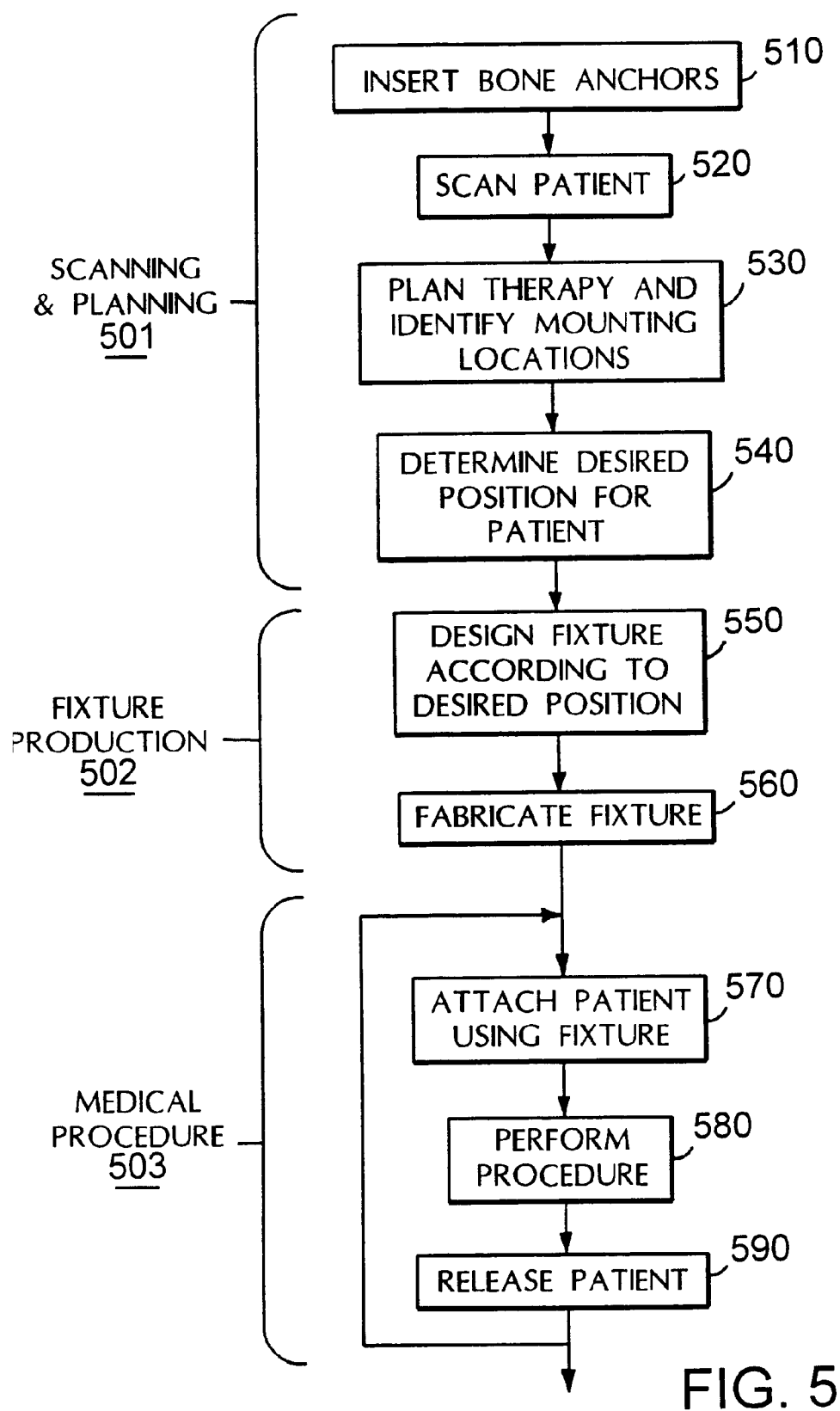
FIG. 5 is a flowchart illustrating design, fabrication, and use of a positioning fixture.

A first embodiment of the invention is used in an exemplary application to fractionated radiotherapy in which the patient is treated in a series of sessions, typically on different days. This use is described in conjunction with a flowchart shown in FIG. 5, which outlines the process. It should be understood that although described in the context of fractionated radiotherapy, this and other embodiments are applicable to positioning a patient relative to a variety of different types of medical apparatuses and to various types of medical procedures. For example, precise predetermined positioning using custom fabricated positioning fixtures is useful for laser surgery, or for robotically controlled surgery.

In this exemplary application, a radiotherapy apparatus directs a relatively narrow beam of radiation through a target in the patient's body from a number of different directions. Essentially the only point in common to the beam paths from the different directions is this target. Therefore the target receives a much higher does of radiation than do points other than the target point, even those on any one of the beam paths. In order to carry out this type of therapy, the radiotherapy apparatus is controlled to direct the radiation beam through the target. In the description that follows related to this embodiment, we assume that we are concerned with a target within the patient's head, although, as is discussed further below, the approach is equally applicable to targets in other parts of the body.

Figure 1A:
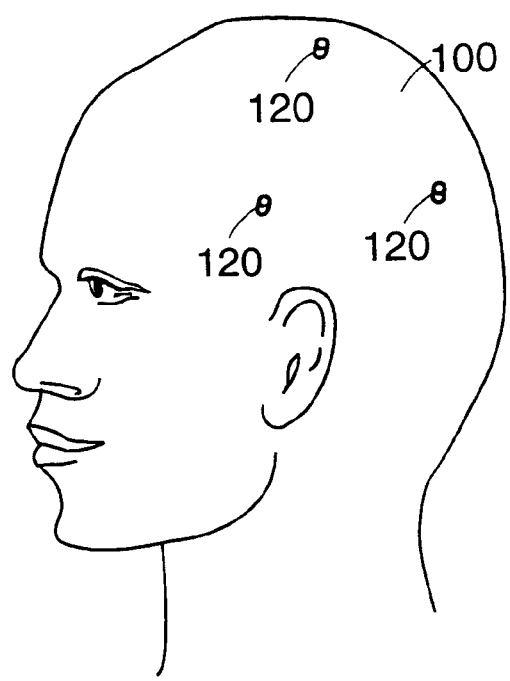
FIGS. 1A–B are diagrams that show scanning markers and bone anchors used to attach the scanning markers to a skull.

Referring to FIG. 1A, in a first phase, a scanning and planning phase (501, FIG. 5), a set of bone anchors 120 is attached to the patient's skull 100 prior to scanning the patient (step 510). In the illustrative example shown in FIG. 1A, three bone anchors 120 are attached to the skull. A greater or smaller number of anchors can also be used, although three or more anchors are preferable. These bone anchors become mounting locations on the patient's body, which provide the means by which the patient's head will later be held in position with the radiotherapy apparatus using the custom fabricated positioning fixture.

Figure 1B:
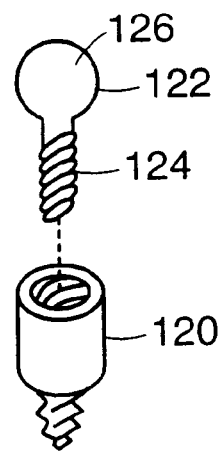

Referring to FIG. 1B, each bone anchor 120 has a threaded opening for accepting threaded bolts or other threaded attachments. Prior to scanning, each threaded opening is used to accept a scanning marker 122. Each scanning marker 122 includes a threaded section 124 attached to a marker portion 126. Marker portion 126 includes a material that will result in a visible image in the scanned image. Various types of scanning techniques can be used, including CT, PET, MRI, SPECT, and laser. The material in the marker portions 126 is chosen depending on the scanning technique that will be used. Preferable, but not necessarily, the bone anchors are made of a material that is invisible in the scanning technique used, and which minimally distorts the scanned image in the vicinity of the anchor.

Figure 2:
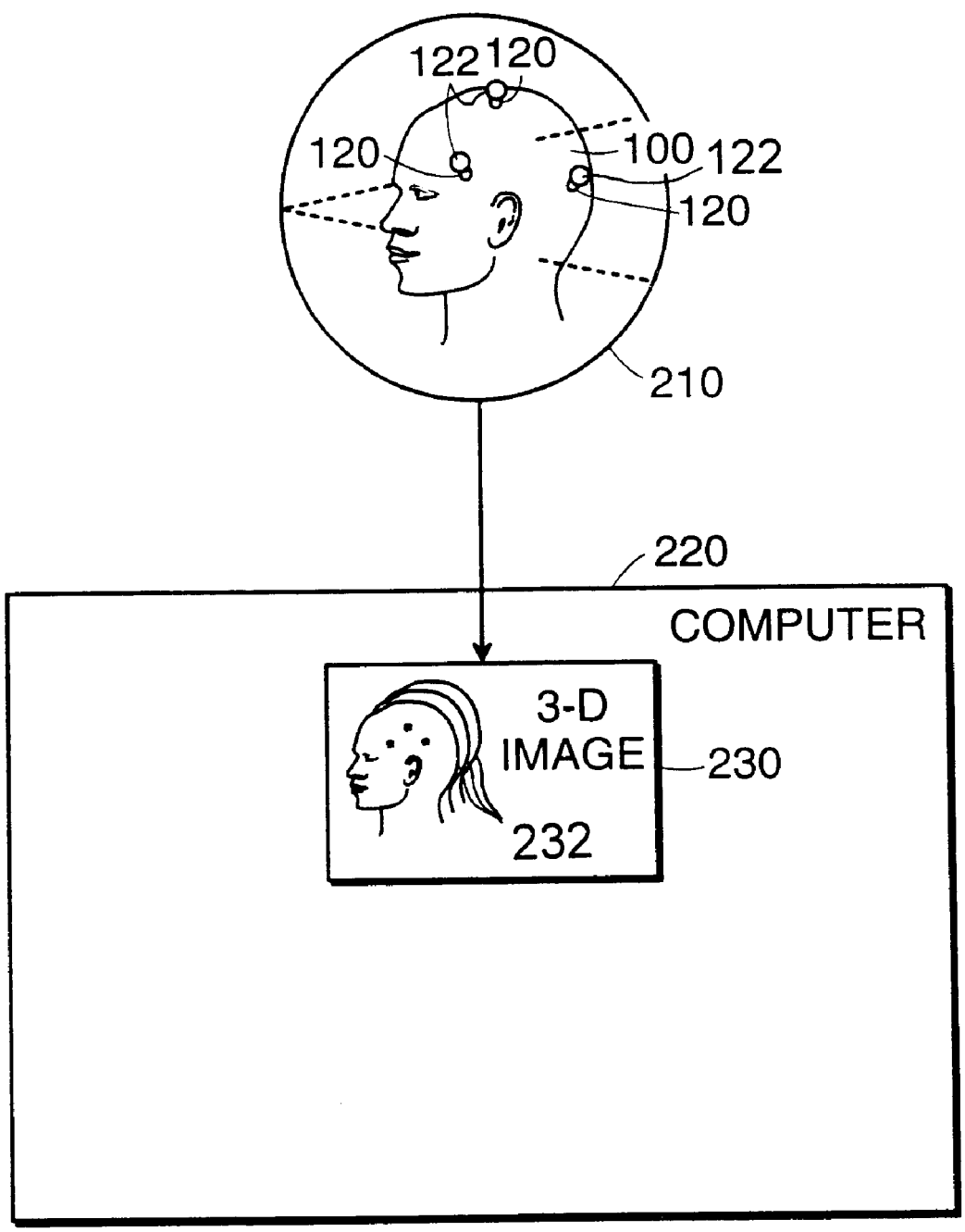
FIG. 2 is a diagram that illustrates a scanning phase.

Referring to FIG. 2, after scanning markers 122 are attached to bone anchors 120, the patient is scanned in a scanner 210 (illustrated schematically) producing a three-dimensional image 230 (step 520). The three-dimensional image is formed as a series of planar sections 232 that are "stacked" to form an image of the volume within the patient. The image is transferred to a computer 220 where it is stored.

After the scanning process is complete, scanning markers 122 are removed from the patient, but bone anchors 120 are left in place. In a typical situation, because the therapy phase of the process will not begin for several hours, or even several days, the patient is allowed to walk around or even allowed to return home at this point.

Figure 3:
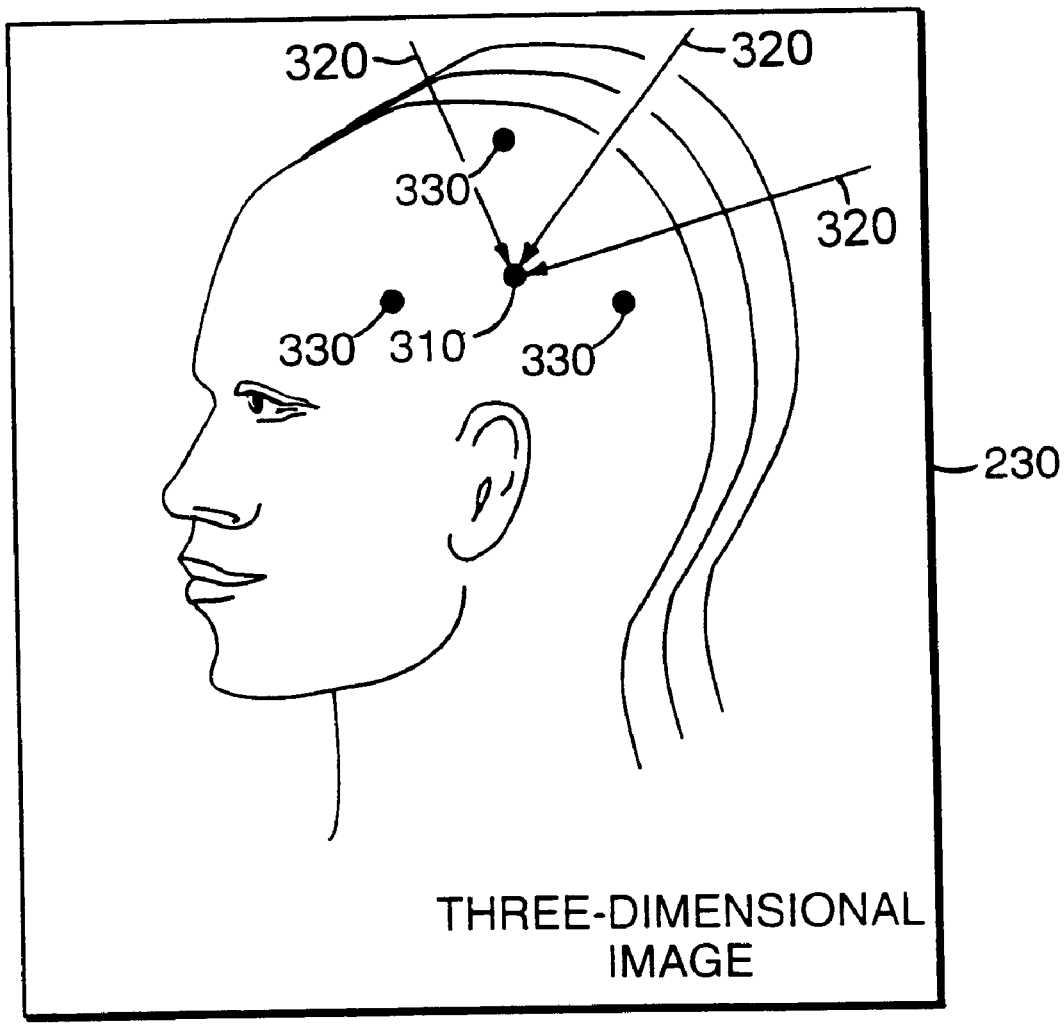
FIG. 3 is a diagram that illustrates a scanned image and located image points.

Referring to FIG. 3, a doctor (or other practitioner) plans the upcoming therapy using a computer display of image 230 using well-known techniques for computer-aided medical planning (step 530). The doctor identifies a target image point 310 in image 230 corresponding to a target point in the body. The three dimensional coordinates of the target image point in the coordinate system of image 230 are stored on the computer. The doctor optionally also identifies a set of desirable beam paths 320 through the target point, for example, that avoid particular critical structures of the brain. Data characterizing these paths is also stored on the computer.

Referring still to FIG. 3, marker image points 330 in image 230 correspond to the marker portions 126 of scanning markers 122 (FIG. 1B). The doctor planning the therapy locates these points using the computer display in a similar manner to locating the target and choosing beam paths. Alternatively, an automated algorithm is inmplemented on computer 220 to locate marker image points 330 based on the image characteristics, such as brightness or shape, of the points. In either case, the coordinates in the image of marker image points 330 are stored on the computer. This data is later used to compute the model of the positioning fixture so that it mates properly with the bone anchors.

Based on the planning, the doctor determines a desired position for the patient relative to the radiotherapy apparatus (step 540). Alternatively, this position is computed automatically based on data characterizing the target position and the desired beam paths.

Figure 4:
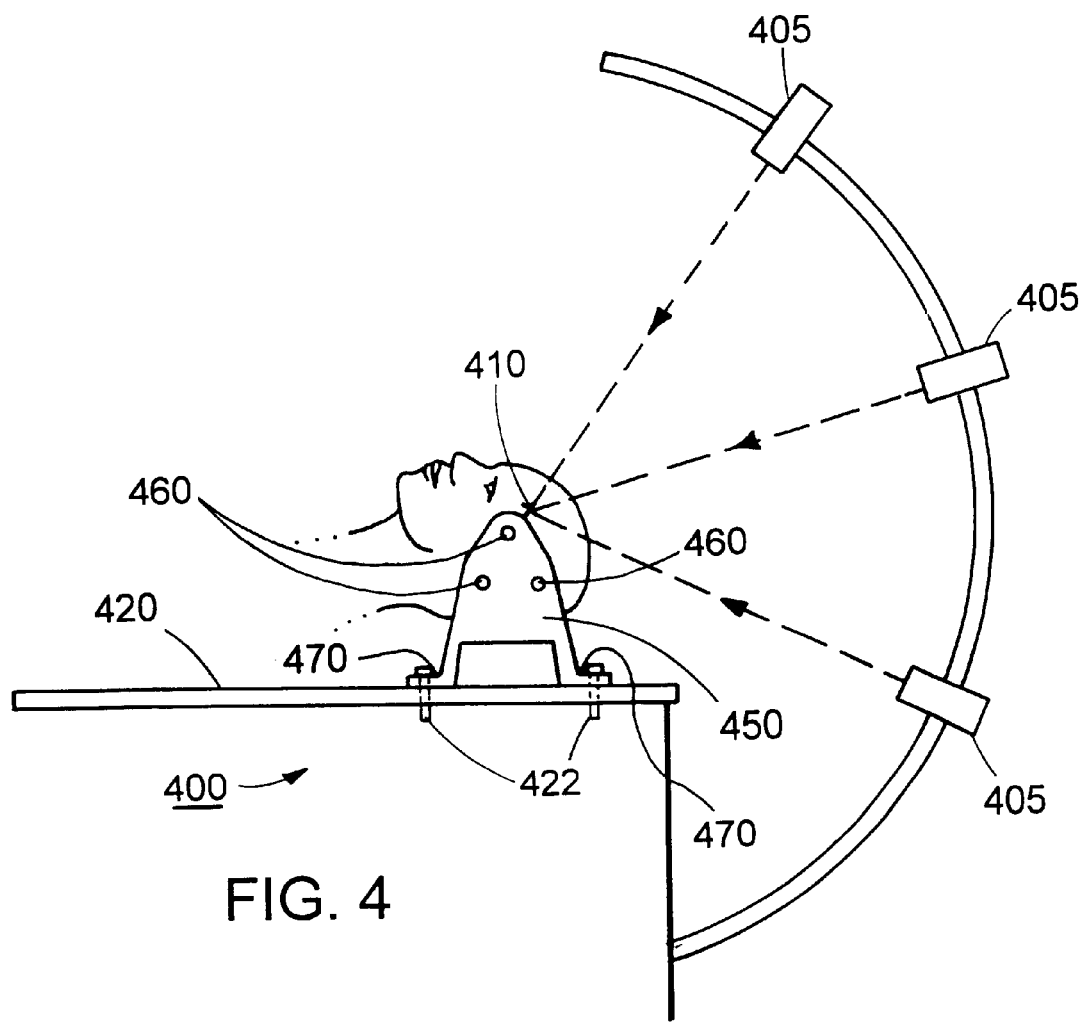
FIG. 4 is a diagram showing a patient fixed in a medical apparatus using a positioning fixture.

In this embodiment, we assume that the patient is to be positioned in the radiotherapy apparatus such that the target is at a pre-determined location within the apparatus. Referring to FIG. 4, radiotherapy apparatus 400 has a radiation emitter 405 that can pivot to direct a beam to a common "focal" point 410, illustrated here as a point that is located above a supporting surface 420. In FIG. 4, radiation emitter 405 is shown in three different orientations. The supporting surface has a number of threaded mounting locations 422 at which the positioning fixture can be attached.

Positioning fixture 450 provides a way of attaching the patient's head to mounting locations 422 so that target 310 is at focal point 410. Based on the data obtained from the scan of the patient and known positions of the threaded mounting points 422 to focal point 410, a computer-aided procedure determines a design for the positioning fixture. That is, the procedure uses the coordinates of the target and of the mounting locations on the body to determine data that characterizes the shape or volume of positioning fixture 450. This shape is such that it has a first set of mounting structures 460 that mate with bone anchors 120 and a second set of mounting structures 470 that mate with the set of threaded mounting locations 422 in the therapy apparatus. In this embodiment, the mounting structures of the positioning fixture include hoses through which bolts are passed to firmly attach the positioning fixture to bone anchors 120 and to supporting surface 420.

In order to orient the mounting structures perpendicularly to the axes of the bone anchors, this approach to designing the positioning fixture make use of knowledge of the orientations as well as the locations of the bone anchors. In the approach described above, as shown in FIG. 1B, a single marking portion 126 is attached in scanning marker 122 to each bone anchor 120. Therefore only the location of each bone anchor is determined by locating the marker images of the scanning markers.

One of several alternative approaches to determining the orientation of the bone anchors is used. First, alternative scanning markers 122 can be used. The alternative scanning markers have two marking portions 126 separated along the axis of the scanning marker. Locating the images of both the marking portions determines the orientation of the bone anchor. A second alternative is to use a normal direction to a surface models of the skull. The surface model of the skull can be computed directly from the scanned image using well-known image processing techniques. A third alternative is to approximate the orientation of the bone anchors by fitting a surface through the locations of the scanning markers.

In a computer-aided or an automated procedure, the desired position for the patient is used to design the positioning fixture (step 550). A computerized procedure converts the design of the positioning fixture into a data specification of a solid model. A solid model is a computer representation of a volume enclosed by a surface surrounding the entire volume. Various types of computer representations of the volume can be used. A common format is an ".stl" file that is used by many computer aided design (CAD) systems. The .stl file includes a set of representations of surface patches that together define a complete surface that encloses the volume. The .stl file for the designed fixture is then used as the specification for fabrication of the fixture. The solid model file is transferred to a rapid prototyping and tooling (RPT) machine. The file can be transferred on a physical medium, such as a magnetic disk, sent over a data network, or used directly on the computer on which is was computed.

A variety of RPT techniques can be used to fabricate the positioning fixture (step 560). In this embodiment, a Fused Deposition Modeling (FDM) machine, such model FMD2000 manufactured by Stratasys, Inc. of Eden Prairie, Minn., is used to make the three dimensional fixture from the . stl file. The FDM machine essentially robotically lays down a long ribbon of extruded material thereby slowly building up the modeled fixture. As material is laid down, it fuses with the previously laid down material making a homogeneous solid. This results in the fixture forming a rigid unitary structure. The process results in a highly accurate fixture, within 5 mil of the specification in the .stl file. Various materials or RPT methods, such as various plastics, laser sintered metals, and CNC machining can also be used. In the embodiment, medical grade ABS is used. Various other materials, such as various plastics, can also be used. For scanning and radiotherapy applications, materials that are transparent to radiation may be used.

As illustrated in FIG. 4, after positioning fixture 450 fabricated, the patient is treated in radiotherapy apparatus 400. In a medical procedure phase (503), in each treatment session, the positioning fixture is first secured to both the patient and the radiotherapy apparatus (step 570). Bolts or other threaded fasteners are inserted through holes in the mounting structures and secured in the bone anchors and in the threaded mounting locations of the apparatus. Then, the treatment is performed with the patient firmly secured in the predetermined position within the radiotherapy apparatus (step 580). After the treatment for the session is completed, the patient is released from the positioning fixture, leaving the bone anchors in place (step 590). This process is repeated on a number of treatment sessions, which can span weeks or even months. At each session, the patient is positioned in precisely the same position. After the final treatment session, the bone anchors can be removed.

In related embodiments, the apparatus is adjustable and does not require that the target be at a specific location. In such an embodiment, the positioning fixture is associated with a data specification of the location of the target relative to a coordinate system that is fixed relative to the positioning fixture. Also, is some embodiments, the target within the body is a volume or a set of points and the apparatus is adjustable to allow treatment of the points of the target.

3 Alternative Mounting Approaches and Fixture Structures

In the embodiment described above, the positioning fixture is attached to bone anchors, which form the mounting location on the body. In alternative embodiments, various alternative mounting arrangements are used.

One alternative approach does not rely on the mounting structure being normal to the axes of the bone anchors. Instead, a ball is mounted on each bone anchor and the fixture has corresponding sockets that mate with the balls. In another alternative, subcutaneous anchors are inserted into the body, for instance, into the skull. Each anchor has a depression, or "dimple," in the center of the end just below the skin. The positioning fixture is designed to accommodate mounting pins that mate with the dimples and which clamp the fixture in place. Such sub-cutaneous anchors may be preferable to exposed bone anchors if an extended duration of therapy is required. Also, in some circumstances, it may not be necessary to remove the anchors once the course of therapy has been completed.

Another alternative does not make use of anchors or other structures being attached to the body to form mounting locations. Rather, the positioning fixture is designed to mate with anatomical contours of the patient's body, which themselves form the mounting locations on the body. For instance, the positioning fixture can form a contoured headrest on which the patient places his or her head during the procedure. In a variant of this procedure, rather than forming a single unitary structure, the positioning fixture is formed on two separate sections that form a clamp that matches the contours of the patient's body. For example, in addition to a first section forming a headrest, a second section can form a clam section that holds the head firmly in place. A wide variety of anatomical contours can be used, including the head, face, jaw, or entire limbs. Also, bone structures (such as the spine) that are exposed in a surgical procedure can be used.

Another alternative to positioning the patient involves designing the positioning fixture to form a "shim" that mates with anatomical contours of the patient's body and provides a mounting structure for attaching to another positioning fixture, which is not necessarily specifically customized for the patient. For example, a shim between the patient's head and a conventional stereotactic frame (a "halo") can provide a means of repeatably attaching the frame. The halo is then attached to the apparatus to position the patient in a predetermined position. In such embodiments in which the custom fabricated positioning fixture forms a shim between the patient and another mechanical structure, the other structure can be selectable and optionally coarsely adjustable, and the customized portion provides fine adjustment.

4 Multiple Positioning Fixtures

In some embodiments, two separate positioning fixtures are fabricated, each for use with a different apparatus, but which both mate with the same mounting locations on the body. For instance, proceeding with the radiotherapy example introduced above, a second positioning fixture is fabricated to position the patient in a scanner, while mounting to the same bone anchors used to secure the patient in the radiotherapy apparatus. The second fixture is designed so that successive three-dimensional scans yield views in which the "slices" of the scan come from the same planes through the patient's body in order to allow direct comparison from scan to scan. For example, the positioning fixture for the scanning apparatus may be designed to reproduce the position in which the patient was originally scanned when the target was identified.

In another embodiment involving multiple scanning apparatuses, multiple positioning fixtures are fabricated, each for a different scanning apparatus. The mounting structures that mate with the mounting locations on the body have the same geometric interrelationship, but mounting structures for mating with the mounting locations of the apparatus are specific to the apparatus. One application on this is to design the positioning fixtures so that two-dimensional images planes from the different scanning apparatuses coincide, thereby allowing direct comparison of the images from the different scanners, or forming of composite images using features obtained using each of the scanners.

It is to be understood that the foregoing description is intended to illustrate and not to limit the scope of the invention, which is defined by the scope of the appended claims. Other embodiments are within the scope of the following claims.

What is claimed is:

1. A method for positioning a body in relation to a medical apparatus using a customized positioning fixture comprising:

providing a three-dimensional scanned image of the body;

determining from the scanned image of the body mounting data that characterizes positions of a plurality of mounting locations on the body;

using the mounting data, computing a digital model of the positioning fixture that characterizes a shape of the positioning fixture such that the shape includes a first plurality of mounting structures that mate with the mounting locations on the body, and a second plurality of mounting structures for attaching the positioning fixture to the medical apparatus;

fabricating the positioning fixture according to the digital model; and fixing the body to the medical apparatus in a predetermined position of the body relative to the medical apparatus, including mating the first plurality of mounting structures with the mounting locations on the body, and attaching the positioning fixture to the medical apparatus using the second plurality of mounting structures.

2. The method of claim 1 wherein fabricating the positioning fixture includes forming a unitary structure using a computer-controlled process.

3. The method of claim 2 wherein forming the unitary structure using a computer-controlled process includes forming said structure using a rapid prototyping and tooling (RPT) technique.

4. The method of claim 1 further comprising:
    after fixing the body to the medical apparatus in the predetermined position, releasing the body from the positioning fixture; and
    repeating the steps of fixing the body to and then releasing the body from the medical apparatus, whereby at each repetition the body is fixed in the same predetermined position relative to the medical apparatus.

5. The method of claim 1 further comprising forming a three-dimensional scanned image of the body and wherein determining the mounting data includes identifying the mounting locations in the scanned image.

6. The method of claim 5 further comprising attaching a plurality of mounting devices to the body prior to forming the scanned image to form the mounting locations on the body.

7. The method of claim 6 wherein attaching the mounting devices includes attaching bone anchors.

8. The method of claim 7 wherein attaching the bone anchors includes attaching subcutaneous bone anchors.

9. The method of claim 5 wherein identifying the mounting locations in the scanned image includes identifying points on an anatomical structure of the body.

10. The method of claim 1 wherein the shape of the positioning fixture forms a plurality of segments that form a clamp which mates with the anatomical structure when the positioning fixture is fixed to the body.

11. The method of claim 1 wherein the medical apparatus is a scanning device.

12. The method of claim 1 further comprising:
    determining a location of a target within the body; and
    using the determined location of the target, determining the predetermined position of the body in order to position the target at a predetermined position relative to medical apparatus when the body is fixed to said apparatus using the positioning fixture.

13. The method of claim 12 wherein the medical apparatus includes a radiation therapy device.

14. The method of claim 1 further comprising:
    determining a second position of the body relative to a second medical apparatus;
    using the mounting data and the determined second position, computing a second digital model of a second positioning fixture;
    fabricating the second positioning fixture according to the second digital model; and
    fixing the body to the second medical apparatus in said second position, including mating the second positioning fixture with the mounting locations on the body and attaching the second positioning fixture to the second medical apparatus.

15. A method for forming a surgical fixture for attaching to a body and providing a reference structure for precisely locating a target within the body, the method comprising:
    computing a digital model of the surgical fixture such that when attached at the mounting location of the body the fixture provides a reference structure in a determined location and orientation with respect to the target within the body, and provides attachment locations for a plurality of tracking markers in determined locations on the surgical fixture;
    fabricating the surgical fixture according to the digital model;
    attaching the surgical fixture to the body;
    attaching the plurality of tracking markers to the surgical fixture at the attachment locations; and
    tracking locations of the tracking markers relative to a remote sensing device.

16. The method of claim 15 further comprising:
    tracking a location of a surgical instrument relative to the remote sensing device; and
    computing a relative position of the surgical instrument to the surgical fixture using the tracked location of the tracking markers and the surgical instrument relative to the remote sensing device.

17. The method of claim 15 further comprising:
    attaching a second surgical fixture at a second mounting location of the body;
    attaching a second plurality of tracking markers to the second surgical fixture;
    tracking locations of the tracking markers attached to the second surgical fixture relative to the remote sensing device; and
    computing a relative position of the mounting locations of the body from the tracked locations of the tracking markers attached to both surgical fixtures.

18. The method of claim 15 wherein the body includes a second mounting location, and the determined structure of the surgical fixture is such that when attached to the mounting locations, the body is held with the mounting locations in a predetermined geometric relationship.

* * * * *